United States Patent [19]

Allen

[11] 4,394,523

[45] Jul. 19, 1983

[54] CATALYTIC HYDROGENATION OF DI (4-AMINOPHENYL) METHANE

[75] Inventor: Gary F. Allen, New Martinsville, W. Va.

[73] Assignee: Mobay Chemical Corporation, Pittsburgh, Pa.

[21] Appl. No.: 269,200

[22] Filed: Jun. 1, 1981

[51] Int. Cl.³ .............................................. C07C 85/24
[52] U.S. Cl. ...................................... 564/451; 564/450
[58] Field of Search ................................. 564/451, 450

[56] References Cited

U.S. PATENT DOCUMENTS

| | | | |
|---|---|---|---|
| 2,494,563 | 1/1950 | Kirk, Jr. et al. | 260/563 |
| 2,606,924 | 8/1952 | Whitman | 260/563 |
| 2,606,925 | 8/1952 | Whitman | 260/563 |
| 2,606,928 | 8/1952 | Barkdoll et al. | 260/563 |
| 3,153,088 | 10/1964 | Arthur | 260/563 |
| 3,155,724 | 11/1964 | Arthur | 260/563 |
| 3,330,850 | 7/1967 | Campbell et al. | 260/453 |
| 3,347,917 | 10/1967 | Arthur | 260/563 |
| 3,361,814 | 1/1968 | Campbell et al. | 260/563 |
| 3,393,236 | 7/1968 | Kuszewski | 260/563 |
| 3,557,180 | 1/1971 | Hoeschele | 260/563 |
| 3,590,002 | 6/1971 | Powers | 252/182 |
| 3,636,108 | 1/1972 | Brake | 260/563 D |
| 3,644,522 | 2/1972 | Brake et al. | 260/563 D |
| 3,676,495 | 7/1972 | Hoeschele | 260/563 R |
| 3,711,550 | 1/1973 | Brake | 260/563 B |
| 3,742,049 | 6/1973 | Komoto et al. | 260/563 D |
| 3,743,677 | 7/1973 | Grosskinsky et al. | 260/563 D |
| 3,766,272 | 10/1973 | Brake | 260/563 B |
| 3,825,586 | 7/1974 | Traumann | 260/501.2 |
| 3,856,862 | 12/1974 | Chung et al. | 564/451 |
| 3,914,307 | 10/1975 | Massie | 260/563 B |
| 3,959,374 | 5/1976 | Brennan et al. | 260/563 B |
| 4,161,492 | 7/1979 | Weissel | 260/563 R |
| 4,226,737 | 10/1980 | Kluger et al. | 252/182 |

FOREIGN PATENT DOCUMENTS 1122609 8/1968 United Kingdom ................ 564/451

OTHER PUBLICATIONS

Chemical Abstracts, vol. 77, 164129q, No. 25, Dec. 18, 1972, Hosaka et al.

*Primary Examiner*—John Doll
*Attorney, Agent, or Firm*—Gene Harsh; Joseph C. Gil; Richard A. Elder

[57] ABSTRACT

The present invention relates to an improved process for the catalytic hydrogenation of di(4-aminophenyl) methane to a liquid di(4-aminocyclohexyl) methane mixture containing from 15 to 40% by weight of the trans, trans isomer. The invention resides in the use of a ruthenium-on-alumina catalyst, the use of an aliphatic alcohol during hydrogenation and the use of ammonia during hydrogenation, with the hydrogenation being conducted under specific process conditions. The hydrogenation reaction is conducted for no more than about sixty minutes at a temperature of from 150° to 217° C. and at a hydrogen pressure of at least 500 psi.

15 Claims, No Drawings

CATALYTIC HYDROGENATION OF DI (4-AMINOPHENYL) METHANE

BACKGROUND OF THE INVENTION

In the production of di(4-aminocyclohexyl)methane by the catalytic hydrogenation of di(4-aminophenyl)methane, essentially three stereoisomers are produced:

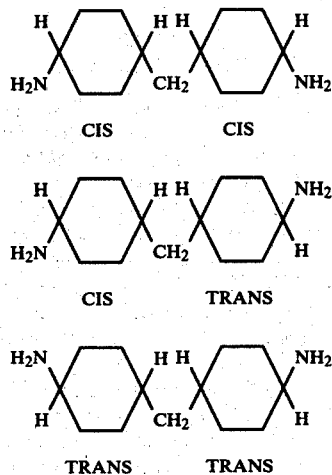

It is known in the art that in order to produce a corresponding isocyanate (via the known phosgenation process) which is liquid and storage stable at room temperature (i.e., from 20° to 25° C.), the mixture of amine stereoisomers used for phosgenation must contain the trans, trans stereoisomer in relatively narrow amounts (typically from 15 to 40% by weight).

Numerous techniques are known in the art for the production of amine mixtures containing the requisite amount of the trans, trans isomer. Typical of these known techniques are those described in U.S. Pat. Nos. 3,153,088; 3,155,724; 3,393,236; 3,644,522; 3,711,550 and 3,766,272. These known techniques generally require the separation of an amine mixture containing the requisite amount of the trans, trans isomer from an amine mixture formed after hydrogenation and containing around 50% by weight of the trans, trans isomer. Processes are known in the art for the production of a di(4-aminocyclohexyl)methane mixture containing the requisite amount of the trans, trans isomer directly from di(4-aminophenyl)methane without the need for an intermediate separation step (see, e.g., U.S. Pat. No. 2,606,928); however, the rates of reaction are much too slow for commercial application.

Numerous processes are known in the art for the production of di(4-aminocyclohexyl)methane from di(4-aminophenyl)methane via catalytic hydrogenation using supported and unsupported ruthenium catalysts. Typical of these processes are those disclosed in U.S. Pat. Nos. 2,494,563; 2,606,924; 2,606,928; 2,606,925; 3,347,917; 3,676,495; 3,959,374; 3,743,677; 3,914,307; 3,825,586; 3,636,108 and 4,161,492. While some of these processes yield an amine mixture containing the trans, trans isomer in an amount necessary to allow for the production of an isocyanate which is liquid and storage stable at room temperature, the rates of reaction are much too slow for commercial use.

Ruthenium-based catalysts have also been described as being useful in the hydrogenation of (a) polycycloaromatic polyamines formed from aniline and formaldehyde (see U.S. Pat. No. 4,226,737); (b) 2,4-bis(p-aminobenzyl)aniline (see U.S. Pat. No. 3,557,180); (c) 2,4'-diaminodiphenylmethane (see U.S. Pat. No. 3,590,002); (d) tolylene diamine/formaldehyde condensates (see U.S. Pat. Nos. 3,330,850 and 3,361,814; and (e) di(4-nitrophenyl)methane (see U.S. Pat. No. 3,742,049). However, none of these processes relate to the present problem, i.e., production of a di(4-aminocyclohexyl)methane containing from 15 to 40% by weight of the trans, trans isomer.

Finally, the use of a solvent and ammonia during the hydrogenation of di(4-aminophenyl)methane in the presence of a ruthenium catalyst is also known (see, e.g., U.S. Pat. Nos. 3,347,917; 3,636,108 and 3,644,522). The '917 patent describes the hydrogenation of di(4-aminophenyl)methane at temperatures of 180° to 300° C. and pressures above 500 psi in the presence of ruthenium, ammonia and solvent to obtain a high yield of di(4-aminocyclohexyl)methane rich in trans, trans isomer (i.e., above 45% by weight). The '108 patent describes the hydrogenation of di(4-aminophenyl)methane at temperatures of from 100° to 300° C. and pressures in excess of 200 psi in the optional presence of ammonia and solvent and in the presence of a supported ruthenium catalyst which has been alkali moderated. In those examples of the '108 patent where the trans, trans content is described as being now (Examples 21, 22 and 27), neither organic solvent nor ammonia were used. Finally, the '522 patent is similar to the '108 patent except that the ruthenium catalyst used is supported on a specific substrate. Like the '108 patent, where the trans, trans content is described as being low (Examples 17, 18 and 19), neither organic solvent nor ammonia were used.

DESCRIPTION OF THE INVENTION

The present invention is directed to the discovery that liquid di(4-aminocyclohexyl)methanes containing from 15% to 40% by weight of the trans, trans isomer can be produced directly from di(4-aminophenyl)methane by hydrogenating in the presence of (i) a ruthenium-on-alumina catalyst, (ii) an aliphatic alcohol, and (iii) ammonia and under specific process conditions. Specifically, the hydrogen pressure must be at least 500 psi, the temperature must be from 150° to 217° C., and the time of hydrogenation must not exceed about sixty minutes.

The ruthenium-on-alumina catalysts used in the present invention are well known in the art and are commercially available, and comprise elementary ruthenium deposited on an alumina carrier. The presently preferred catalyst is available from Engelhard and comprises 5% by weight ruthenium on an alumina carrier.

In conducting the process of the invention, the procedures commonly used in the art are employed, the only requirements being the presence of the alcohol and ammonia and the pressure, temperature and time conditions noted above.

The hydrogenation must be conducted in the presence of an aliphatic alcohol. The aliphatic alcohols used in the present invention include any $C_1$ to $C_{10}$ aliphatic alcohol. Suitable specific alcohols include methanol, ethanol, n-propanol, isopropanol and the like. The presently preferred solvent is methanol. The amount of alcohol must be at least 25% by weight based on the total weight of alcohol and starting diamine. The upper limit on the amount of solvent is dictated by the economics of the process, and will generally not exceed 60% by weight based on the total weight of alcohol and starting diamine. The preferred range of alcohol is from 30% to 50% by weight based on the weight of alcohol and starting diamine. p Ammonia must also be present during the hydrogenation reaction. In general, the amount of ammonia used is such that the molar ratio of ammonia to starting diamine is from 0.5:1 to 10:1. The ammonia is preferably used in an amount such that the molar ratio noted is from 0.5:1 to 5:1 and most preferably about 1:1. The higher amounts of ammonia noted are not generally preferred since higher pressures are generally necessary.

The amount of catalyst employed is such that the amount of ruthenium is at least 0.05% by weight of the starting diamine, is preferably from 0.1% to 3% by weight, and is most preferably from 0.1% to 1% by weight. As noted, the amount of catalyst should be at least 0.05%. Economics generally dictate the upper limit since the catalyst is relatively expensive and since little practical advantage is gained by using relatively large amounts.

In general, the materials are mixed and added to the reactor in a batch process but, of course, a continuous process could also be used.

The hydrogenation is conducted at a temperature of from 150° to 217° C., and preferably from 170° to 200° C. The exact choice of temperature in any given instance is a function of the reaction rate and the trans, trans content desired. In general, the higher the temperature, the faster the reaction rate and the higher the trans, trans content of the final product. Thus, the temperature will be generally selected within the range noted to yield the best balance of reaction time and trans, trans content.

The hydrogenation pressure employed in the process of the invention must be maintained at at least 500 psi, and will generally be from about 1500 psi to 4000 psi. Of course, the pressures used are dependent on the equipment used and could be as high as 8000 psi or higher. In general, it has been found that the yield will increase with increasing pressure.

The progress of the hydrogenation reaction is followed readily by observation of the amount of hydrogen taken up by the reaction mixture and the hydrogenation is terminated at the point at which the theoretical quantity of hydrogen has been absorbed. In general, under the conditions noted, the total hydrogenation time will not exceed about sixty minutes and will typically be from about 10 to 50 minutes. Longer reaction times, particularly at higher temperatures, generally causes an increase in the trans, trans content. Following hydrogenation, the catalyst is separated from the solution of reduced material and the material is distilled to isolate the di(4-aminocyclohexyl)methane.

The invention is further illustrated, but is not intended to be limited by the following examples in which all parts and percentages are by weight unless other specified.

EXAMPLES
EXAMPLES 1 THROUGH 14

200 parts of di(4-aminophenyl)methane, 200 parts of a methyl alcohol solution which contained about 16 parts of ammonia, and the amount of catalyst noted in Table 1 were added to a high pressure autoclave. The catalyst used was an Engelhard ruthenium-on-alumina catalyst containing 5% ruthenium. The autoclave was sealed and pressurized to the pressure noted in Table 1, and the contents were heated to the temperatures noted in Table 1. The hydrogenation times were as set forth in Table 1. The contents of the autoclave were removed and vacuum filtered and then distilled to strip off the methyl alcohol and low boiling products. The resultant hydrogenated products (taken as overhead) were then analyzed for yield and trans, trans content with the results being set forth in Table 1. Examples 6 and 11 through 14 are comparison examples and do fall under the scope of the present invention.

TABLE 1

| Example | Catalyst PBW | % by wt. RuMetal | Pressure PSI | Temperature °C. | Hydrogenation Time, minutes | 3% determined by HPLC Yield | % trans,trans |
|---|---|---|---|---|---|---|---|
| 1 | 15 | 0.5 | 2000 | 177 | 45 | 81 | 23 |
| 2 | 30 | 1 | 4000 | 177 | 20 | 100 | 38 |
| 3 | 30 | 1 | 4000 | 177 | 23 | 83 | 23 |
| 4 | 5 | 0.13 | 4000 | 180 | 45 | 85 | 26 |
| 5 | 5 | 0.13 | 4000 | 180 | 50 | 98 | 32 |
| 6 | 30 | 1 | 1500 | 200 | 120 | 58 | 55 |
| 7 | 15 | 0.5 | 4000 | 200 | 10 | 89 | 26 |
| 8 | 15 | 0.5 | 1500 | 216 | 40 | 62 | 41 |
| 9 | 15 | 0.5 | 1500 | 216 | 44 | 91 | 40 |
| 10 | 15 | 0.5 | 4000 | 217 | 15 | 88 | 36 |
| 11 | 5 | 0.13 | 4000 | 220 | 15 | 77 | 54 |
| 12 | 30 | 1 | 4000 | 220 | 32 | 93 | 46 |
| 13 | 15 | 0.5 | 1000 | 230 | 44 | 38 | 55 |
| 14 | 30 | 1 | 2000 | 230 | 24 | 87 | 46 |

What is claimed is:

1. A process for the catalytic hydrogenation of di(4-aminophenyl)methane to a liquid di(4-aminocyclohexyl)methane containing from 15% to 40% by weight of the trans, trans isomer comprising hydrogenating di(4-aminophenyl)methane in the presence of (i) a ruthenium-on-alumina catalyst (ii) at least 25% by weight of an aliphatic alcohol selected from the group consisting of methanol, ethanol, n-propanol, and isopropanol, based on the weight of the total weight of the di(4-aminophenyl)methane and the alcohol, and (iii) ammonia, the amount of ammonia present being such that the molar ratio of ammonia to di(4-aminophenyl)methane is from 0.5:1 to 10:1, the hydrogenation being conducted at a hydrogen pressure of at least 500 psi, at a temperature of from 150° C. to 217° C., and for a time not exceeding 60 minutes.

2. The process of claim 1 wherein said alcohol is methanol.

3. The process of claim 4 wherein the pressure is at least 1500 psi.

4. A process for the catalytic hydrogenation of di(4-aminophenyl)methane to a liquid di(4-aminocyclohexyl)methane containing from 15% to 40% by weight of the trans, trans isomer comprising hydrogenating di(4-aminophenyl)methane in the presence of (i) a ruthenium-on-alumina catalyst, (ii) at least 25% by weight of an aliphatic alcohol, based on the weight of the total weight of the di(4-aminophenyl)methane and the alcohol, and (iii) ammonia, the amount of ammonia present being such that the mol ratio of ammonia to di(4-aminophenyl)methane is from 0.5:1 to 10:1, the hydrogenation being conducted at a hydrogen pressure of from about 1500 to 4000 psi, at a temperature of from 150° C. to 217° C., and for a time not exceeding sixty minutes.

5. The process of claim 4 wherein said alcohol contains from 1 to 10 carbon atoms.

6. The process of claim 2, wherein said alcohol is methanol.

7. The process of claim 4 wherein the amount of alcohol is from 25 to 60% by weight.

8. The process of claim 7 wherein the amount of alcohol is from 30 to 50% by weight.

9. The process of claim 4 wherein said mol ratio is from 0.5:1 to 5:1.

10. The process of claim 9 wherein said mol ratio is about 1:1.

11. The process of claim 4 wherein the amount of said catalyst is such that the amount of ruthenium is at least 0.05% by weight of the di(4-aminophenyl)methane.

12. The process of claim 11 wherein the amount of ruthenium is from 0.1 to 3% by weight of the di(4-aminophenyl)methane.

13. The process of claim 12 wherein the amount of ruthenium is from 0.1 to 1% by weight of the di(4-aminophenyl)methane.

14. The process of claim 4 wherein the temperature is from 170° to 200° C.

15. The process of claim 4 wherein said time is between ten and fifty minutes.

* * * * *